(12) United States Patent
Inaba et al.

(10) Patent No.: US 8,545,686 B2
(45) Date of Patent: Oct. 1, 2013

(54) ELECTROPHORETIC APPARATUS AND ELECTROPHORETIC METHOD

(75) Inventors: Ryoji Inaba, Hitachinaka (JP); Tomoyuki Sakai, Kokubunji (JP); Motohiro Yamazaki, Mito (JP); Takashi Gomi, Hitachinaka (JP); Kazumichi Imai, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 1342 days.

(21) Appl. No.: 11/397,890

(22) Filed: Apr. 5, 2006

(65) Prior Publication Data

US 2006/0231400 A1 Oct. 19, 2006

(30) Foreign Application Priority Data

Apr. 5, 2005 (JP) ................. 2005-108962

(51) Int. Cl.
*G01N 27/453* (2006.01)
*G01N 27/447* (2006.01)

(52) U.S. Cl.
USPC .......................................... 204/601; 204/451

(58) Field of Classification Search
USPC ............... 204/451, 452, 455, 601, 603, 605; 422/70
See application file for complete search history.

(56) References Cited

U.S. PATENT DOCUMENTS

| | | | |
|---|---|---|---|
| 4,832,815 A * | 5/1989 | Kambara et al. | 204/612 |
| 5,290,419 A * | 3/1994 | Kambara et al. | 204/612 |
| 5,312,535 A | 5/1994 | Waska | |
| 5,534,703 A * | 7/1996 | Kambara et al. | 250/458.1 |
| 5,582,705 A | 12/1996 | Yeung et al. | |
| 5,741,412 A | 4/1998 | Dovichi et al. | |
| 5,833,827 A | 11/1998 | Anazawa et al. | |
| 5,938,908 A * | 8/1999 | Anazawa et al. | 204/603 |
| 6,319,705 B1 | 11/2001 | Tanaka | |
| 6,808,610 B2 * | 10/2004 | Inaba et al. | 204/603 |
| 2001/0040094 A1* | 11/2001 | Inaba et al. | 204/603 |
| 2001/0040096 A1* | 11/2001 | Yamamoto et al. | 204/604 |
| 2004/0003997 A1* | 1/2004 | Anazawa et al. | 204/601 |
| 2004/0021078 A1* | 2/2004 | Hagler | 250/339.13 |
| 2004/0200723 A1* | 10/2004 | Sakai et al. | 204/451 |

FOREIGN PATENT DOCUMENTS

| | | |
|---|---|---|
| JP | 09-096623 | 4/1997 |
| JP | 09-152418 | 6/1997 |
| JP | 09-243598 A2 | 9/1997 |
| JP | 09-288088 | 11/1997 |

(Continued)

OTHER PUBLICATIONS

Kostichka, A. J.; et al. High Speed Automated DNA Sequencing in Ultrathin Slab Gels, Bio/Technology, vol. 10, 1992, pp. 78-81.*
Takahashi, S.; et al. Multiple Sheath-Flow Gel Capillary-Array Electrophoresis for Multicolor Fluorescent DNA Detection, Anal. Chem. 1994, vol. 66, pp. 1021-1026.*

(Continued)

*Primary Examiner* — J. Christopher Ball
*Assistant Examiner* — Gurpreet Kaur
(74) *Attorney, Agent, or Firm* — McDermott Will & Emery LLP

(57) ABSTRACT

The present invention relates to detection of an emission spectrum by irradiating excitation light onto a plurality of electrophoretic paths and dispersing fluorescent light output from the electrophoretic paths in a direction approximately vertical to an electrophoretic direction. According to the invention, since an emission spectrum to be detected does not substantially change over time, it becomes possible to make observed emission spectrums completely correspond to various fluorescent dyes or various bases.

9 Claims, 8 Drawing Sheets

(56) References Cited

FOREIGN PATENT DOCUMENTS

| JP | 2000-283960 A2 | 10/2000 |
| JP | 2004-144479 | 5/2004 |
| JP | 2004-325436 | 11/2004 |
| JP | 2005-338100 | 12/2005 |

OTHER PUBLICATIONS

Japanese Notice of Rejection issued in Japanese Patent Application No. JP 2005-108962, dated Nov. 24, 2009.

* cited by examiner

PRIOR ART
FIG. 3
A
PRIOR ART
FIG. 3
B
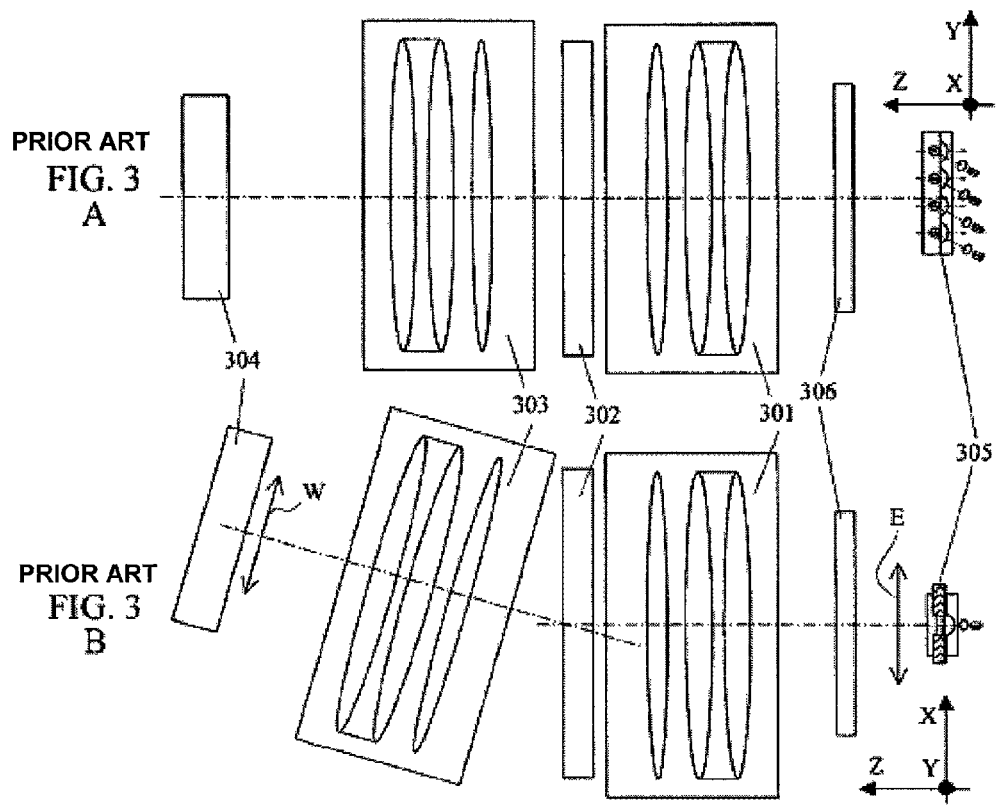
PRIOR ART
FIG. 3 C
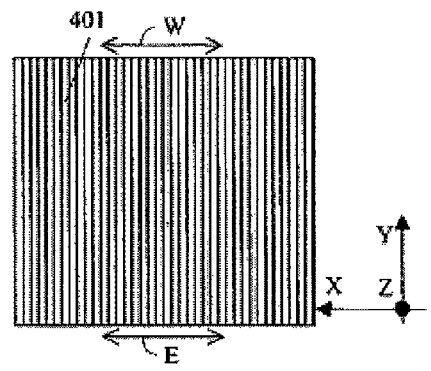
PRIOR ART
FIG. 3 D
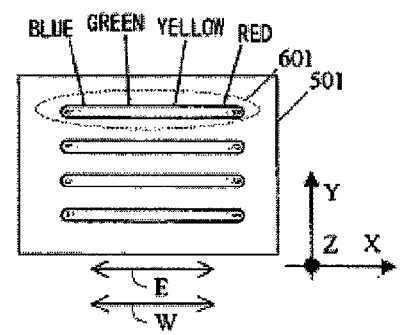

FIG. 4 A
FIG. 4 B
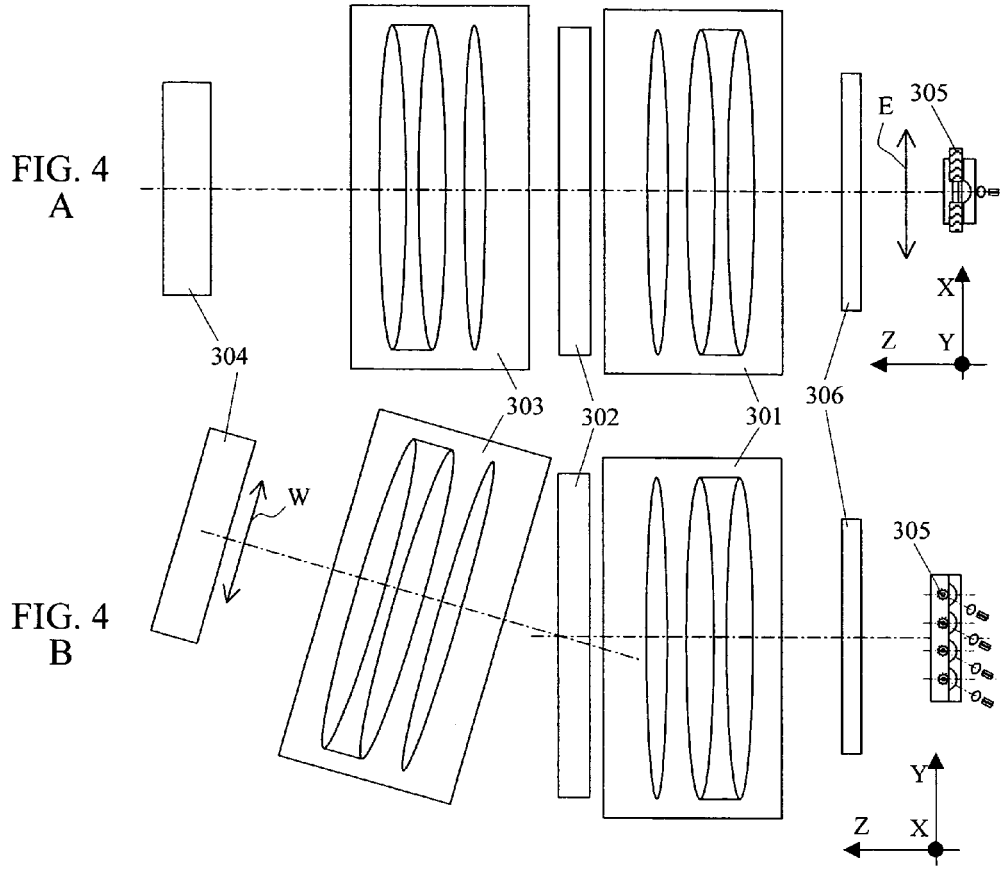
FIG. 4 C
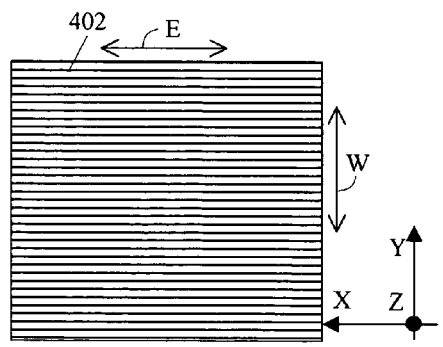
FIG. 4 D
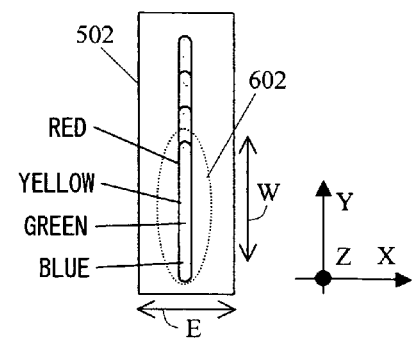

ELECTROPHORETIC APPARATUS AND ELECTROPHORETIC METHOD

BACKGROUND OF THE INVENTION

1. Field of the Invention

The present invention relates to an electrophoretic apparatus for separating and analyzing a nucleic acid, a protein and the like by using an electrophoretic method, and in particular, to a fluorescent detection technique of an electrophoretic apparatus.

2. Description of the Related Art

A capillary electrophoretic apparatus is disclosed in Japanese Patent Application Laid-Open (JP-A) No. 2004-144479. The capillary electrophoretic apparatus uses an electrophoretic method, in which a capillary composed of a quartz tube and a polymer film covering the quartz tube is used, in order to determine the base sequence and the base length of a DNA. A sample including the DNA to be measured is injected into a separation medium, which is made of polyacrylamide and the like and held in the quartz capillary, and a voltage is applied to both ends of the capillary. A DNA composite contained in the sample moves within the capillary and is separated according to the molecular weight, and DNA bands are generated within the capillary. A fluorescent dye is applied onto each of the DNA bands, and the fluorescent dye develops color by laser beam irradiation. Then, the fluorescent dye is read out by a fluorescence measurement unit so as to determine the sequence of the DNAs. Separation and analysis of the protein can be performed in the same manner so as to examine the structure of the protein.

A method of irradiating a light beam onto a sample, which is disclosed in JP-A No. 2004-144479, is as follows. That is, a laser beam is irradiated onto one capillary, which is located at one side end of a capillary array composed of a plurality of capillaries arranged on a flat substrate, or two capillaries, which are located at both side ends of the capillary array, and the laser beam sequentially propagates to adjacent capillaries so as to traverse the capillary array. In addition, a fluorescent detection method is as follows. That is, an image of a laser beam irradiation unit located on the capillary array is formed on a two-dimensional CCD by a condensing lens, a transmissive diffraction grating, and an imaging lens. Of the two axes on the two-dimensional CCD, one is an axis on which emission points of the plurality of capillaries are arrayed, and the other orthogonal to the one is a wavelength dispersion axis made due to the transmissive diffraction grating. In this way, an emission spectrum output from each of the capillaries is formed on the two-dimensional CCD.

In a conventional capillary electrophoretic apparatus, excitation light is irradiated onto a capillary, fluorescent light which is output from a DNA band that moves within the capillary is dispersed according to the wavelength by a diffraction grating, and the wavelength-dispersed fluorescent light is detected by a two-dimensional optical detector, thereby obtaining an emission spectrum.

However, in the conventional capillary electrophoretic apparatus, when the electrophoretic direction (that is, the movement direction of a DNA band in an irradiation region of the excitation light) and the wavelength dispersion direction of the fluorescent light are the same, the emission spectrum detected by the two-dimensional optical detector substantially changes over time. As a result, the analysis precision becomes worse.

In other words, when the electrophoretic direction and the wavelength dispersion direction of the fluorescent light are the same, since the wavelength-dispersed fluorescent light moves in the wavelength dispersion direction while the DNA band passes through the irradiation region of the excitation light, a signal obtainable by the two-dimensional detector changes. Accordingly, at a time when the DNA band passes through the excitation light, the wavelength of an emission spectrum obtainable by the two-dimensional detector substantially changes over time.

In the electrophoretic analysis, a plurality of fluorescent dyes is used and each of the fluorescent dyes corresponds to each of the four kinds of bases. When the emission spectrum substantially changes over time, it is difficult for the observed emission spectrums to completely correspond to various fluorescent dyes or various bases. That is, when each base corresponds to each component of the emission spectrum, a residual component (quasi peak) that does not correspond to a base is generated, which causes the analysis precision to deteriorate.

SUMMARY OF THE INVENTION

Accordingly, it is an object of the present invention to make observed emission spectrums completely correspond to various fluorescent dyes or various bases in electrophoretic analysis using a plurality of electrophoretic paths.

The present invention relates to detection of an emission spectrum by irradiating excitation light onto a plurality of electrophoretic paths and dispersing fluorescent light output from the electrophoretic paths in a direction approximately vertical to an electrophoretic direction.

According to the invention, since an emission spectrum to be detected does not apparently change over time, it is possible to make observed emission spectrums completely correspond to various fluorescent dyes or various bases.

BRIEF DESCRIPTION OF THE DRAWINGS

FIGS. 3A to 3D are views illustrating the relationship between the configuration of an optical detection system and an image on a two-dimensional detector in a conventional capillary electrophoretic apparatus;

FIGS. 4A to 4D are views illustrating the relationship between the configuration of a optical detection system and an image on a two-dimensional detector in a capillary electrophoretic apparatus according to a first embodiment of the invention;

DESCRIPTION OF THE PREFERRED EMBODIMENTS

Hereinafter, the characteristic and advantages of the invention will be described with reference to the accompanying drawings. Here, the drawings are referred only for the convenience of explanation and do not limit the invention.

Figure 1:
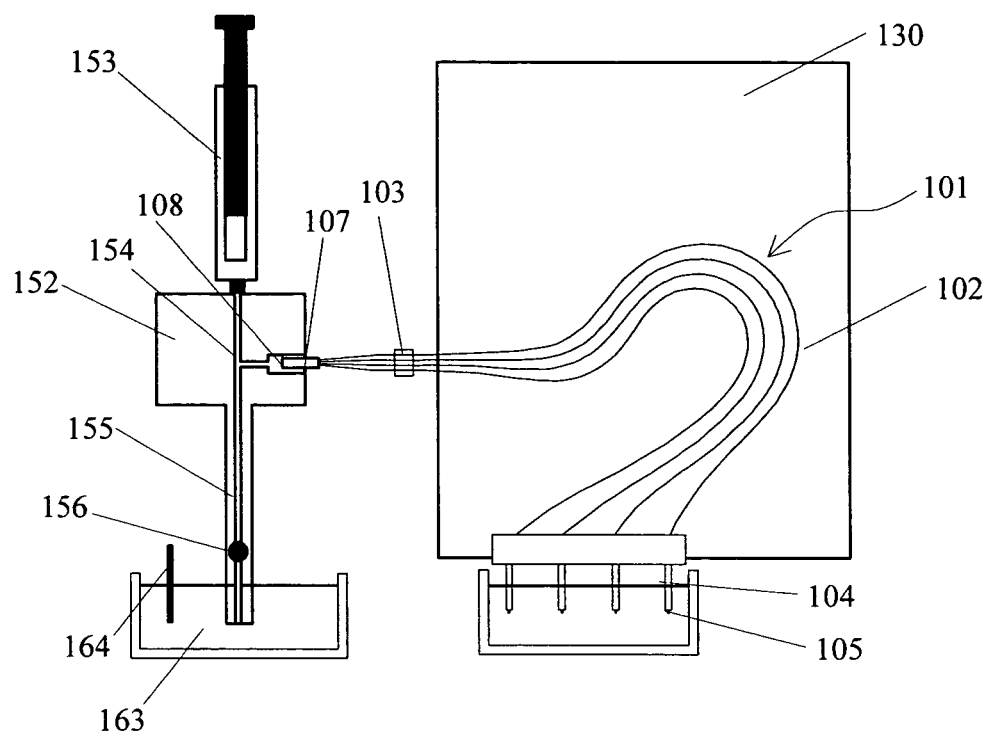
FIG. 1 is a view schematically illustrating a capillary electrophoretic apparatus according to the invention.

FIG. 1 is a view schematically illustrating an electrophoretic apparatus according to an embodiment of the invention (hereinafter, referred to as "present apparatus"). The present apparatus uses a plurality of capillaries in which an electrophoretic medium is filled, injects a sample into each capillary, and electrophoretically separates and analyzes a sample component of the sample. The present apparatus basically includes a capillary array, an illumination optical unit, an optical detection unit, an auto sampler unit, an electrophoretic medium filling unit, a power supply unit, and a temperature control unit.

A capillary array 101 is a detachable and replaceable member composed of a plurality of capillaries 102. The quality of the capillary array 101 deteriorates over a predetermined number of analyses, and the capillary array 101 is replaced with a new one when the separation ability of the capillary array 101 is reduced. In addition, when a measuring method needs to be changed, it is possible to adjust the length of the capillary 102 by replacing the capillary array 101 with a new capillary array composed of capillaries having different lengths from the old capillaries 102. The capillary array 101 includes a sample injection part 104 that injects a sample into the capillary 102, an irradiation part 103 that irradiates excitation light onto an electrophoretically separated sample, and a capillary head 107 that ties the capillaries together.

The capillary 102 is a slender tube whose internal diameter is several tens of micrometers to several hundreds of micrometers and external diameter is several hundreds of micrometers, and a surface of the capillary 102 is coated so as to improve the strength. An electrophoretic medium is filled inside of the capillary 102, and thus an electrophoretic path is formed. A sample can be electrophoretically separated by applying a voltage to both ends of the electrophoretic path.

In the present embodiment, a quartz pipe is used in which the external surface is coated with polyimide, and the overall length, the external diameter and the internal diameter of the quartz pipe are 40 cm, 360 µm, and 50 µm, respectively. Four capillaries 102 tied together forms the capillary array 101. In addition, the number of capillaries 102 is not limited to four. For example, 1, 8, 16, 96, 192, or 384 capillaries 102 may be used. In addition, if necessary, the capillary 102 may be coated with a resin other than polyimide.

In the sample injection part 104, the sample injection end 105 of the capillary 102 is disposed to correspond to wells of a sample container. Accordingly, a plurality of samples held in the respective wells can be injected into the electrophoretic path.

In the present embodiment, a front end of the capillary 102 is inserted into a hollow electrode so as to form the sample injection end 105, thereby forming the sample injection part 104. In the sample injection end 105, the front end of the capillary 102 slightly protrudes from the hollow electrode. The hollow electrode composed of a stainless pipe is electrically connected to a high voltage power supply. By immersing the sample injection end 105 into a sample and applying a voltage, the sample can be electrophoresed so as to be injected into the capillary 102. In addition, a method of inject-ing a sample is not limited to the electrophoretic method, but the sample may be injected into the electrophoretic path by using a pressure or a divided injection method.

On the irradiation part 103 about 30 cm away from the sample injection part 104 of the capillary 102, the polyimide film is removed. The illumination optical unit illuminates excitation light onto the irradiation part 103, and the optical detection unit detects fluorescent light from the irradiation part 103. When the excitation light is illuminated onto an electrophoretically separated sample component in the irradiation part 103, a fluorescent material marked on the sample component emits fluorescent light having a wavelength according to the sample component. By detecting the fluorescent light, it is possible to obtain the sequence of bases and the length of bases in a DNA.

The capillary head 107 ties the four capillaries together and can be detached from a main body of the present apparatus. The capillary head 107 can be connected to a polymer filling block 152 by pressure in an air tight manner. In addition, a new electrophoretic medium can be filled into the capillary 102 through a termination part 108 by using the electrophoretic medium filling unit.

The auto sampler unit is a mechanism that transports various containers, such as a sample container used in the electrophoretic analysis, to a predetermined position, for example, immediately below the sample injection part 104 and holds the transported various containers. The auto sampler unit in the present embodiment transports a sample container, a buffer container, a washing container, and a waste solution container by a robot arm having claws.

The robot arm includes claws on which the various containers are fixed, and the robot arm can move in a three-dimensional manner. In this way, the various containers stored in a predetermined location can be transported immediately below the sample injection part 104, can be held at the position for a predetermined period of time, and can be returned to the predetermined location.

The buffer container is a container that holds a buffer solution into which the sample injection end 105 is immersed. In order to immerse the sample injection end 105 into the buffer solution during the electrophoretic analysis, the buffer solution is transported immediately below the sample injection part 104. In addition, when the present apparatus is not operating, the buffer solution is transported immediately below the sample injection part 104 in the same manner as when the electrophoretic analysis is performed, and accordingly, the sample injection end 105 is immersed into the buffer solution. As a result, the electrophoretic medium included in the capillary 102 can be prevented from being dried.

The washing container is a container that holds a washing solution for washing the sample injection end 105 and is transported immediately below the sample injection part 104 after an electrophoretic medium filling, a preliminary electrophoresis, and a sample injection. By immersing the sample injection end 105 into the washing solution held in the washing container, the sample injection end 105 is washed, and thus it is possible to prevent the sample injection end 105 from being contaminated.

The waste solution container is a container that holds a waste electrophoretic medium and is transported immediately below the sample injection end 105 when the electrophoretic medium is filled and then receives the waste electrophoretic medium discharged from the sample injection part 104 when the electrophoretic medium is filled.

The sample container is a container that holds a plurality of samples each having a very small amount, and the sample container is transported immediately below the sample injection part 104 when a sample is injected. In the present embodiment, the sample container is formed by placing a septa, which is a sheet made of resin, on a sample plate and pinching the septa and the sample plate with a holder and a clip, the sample plate including wells of 24 rows by 16 columns, each well holding a sample of several 10 µl. As a sample, there is used a solution which is fluorescently marked so as to discriminate among, for example, four kinds of nucleotide base molecules and which includes a plurality of nucleic acids each having a proper length (size). The septa has a through hole, which is normally sealed, at a position corresponding to a well, in order to prevent a sample held in the well from evaporating and to make the sample injection end 105 and the sample come in contact with each other at the time of a sample injection. In addition, a protective film may be attached on an upper surface of the septa so as to prevent the sample from evaporating. In addition, the holder and the clip are integrally formed with the sample plate or the septa interposed therebetween, thereby forming a sample container which can be transported by a robot arm.

The electrophoretic medium filling unit is a mechanism for filling a polymer, which is an electrophoretic medium, into the capillary 102. The electrophoretic medium filling unit in the present embodiment includes a polymer filling block 152, a syringe 153, a tube 155, and a solenoid valve 156 and can automatically fill a new electrophoretic medium into the capillary 102 before starting the analysis.

The polymer filling block 152 having a polymer flow channel 154 is connected to the syringe 153 and the tube 155, and the capillary head 107 can be detached from the polymer filling block 152. The capillary head 107 maintains pressure in an air tight manner and is mounted on the polymer filling block 152. The polymer flow channel 154 is in communication with the syringe 153 filled with the electrophoretic medium and the tube 155 including the solenoid valve 156. The other end of the tube 155 is immersed in a buffer solution held in a positive-polarity buffer container 163.

When the electrophoretic medium is filled into the capillary 102, the waste solution container is disposed immediately below the sample injection part 104, the solenoid valve 156 is closed, and a plunger of the syringe 153 is pressed. Then, the electrophoretic medium held in the syringe 153 is injected from the termination part 108 into the capillary 102 through the polymer flow channel 154. In addition, a waste electrophoretic medium in the capillary 102 is discharged from the sample injection end 105 to be received in the waste solution container.

The power supply unit is a mechanism that applies a voltage to an electrophoretic path formed by an electrophoretic medium in the capillary 102 and can electrophorese the sample. The power supply unit in the present embodiment is electrically connected to the hollow electrode and a positive electrode 164 and includes a high voltage power supply capable of generating a high voltage of about 15 kV.

At the time of the sample injection, the capillary 102, the polymer flow channel 154, and the tube 155 are filled with the electrophoretic medium, the sample injection end 105 is immersed in the sample held in the well of the sample container, and the solenoid valve 156 is opened. As a result, an electrical path composed of the hollow electrode, the sample held in the well, the capillary 102, the polymer flow channel 154, the tube 155, the buffer solution held in the positive-polarity buffer container 163, and the positive electrode 164 is formed. In addition, a pulse voltage is applied to the electrical path with the hollow electrode as a negative potential and the positive electrode 164 as a positive potential. Thereby, a sample component, which is negatively charged, held in the well, for example, a DNA sample is injected from the sample injection end 105 into the electrophoretic path.

Furthermore, at the time of the electrophoretic analysis, the sample injection end 105 is immersed in the buffer solution held in the buffer container, unlike at the time of sample injection. As a result, an electrical path composed of the hollow electrode, the buffer solution held in the buffer container, the capillary 102, the polymer flow channel 154, the tube 155, the buffer solution held in the positive-polarity buffer container 163, and the positive electrode 164 is formed. In addition, unlike at the time of the sample injection, a high voltage of 15 kV is applied to the electrical path. Thereby, an electrical field is generated in the direction from the irradiation part 103 to the sample injection part 104, and a sample component, which is negatively charged, injected into the electrophoretic path, is electrophoresed in the direction of the irradiation part 103.

The temperature control unit is a mechanism that controls the temperature of the electrophoretic path which affects the electrophoretic speed of the sample component. The temperature control unit in the present embodiment includes the capillary 102 accommodated within a constant-temperature bath 130. In addition, a blower mechanism such as a fan makes air, which is maintained at a predetermined temperature by a temperature control mechanism such as a Peltier module, circulating within the constant-temperature bath 130, and thus the capillary 102 is maintained at a predetermined temperature.

Hereinafter, the basic procedure of the electrophoretic analysis will be described. The basic procedure of the electrophoretic analysis is composed of a preliminary preparation, an electrophoretic medium filling, a preliminary electrophoresis, a sample injection, and an electrophoretic analysis. An operator of the present apparatus sets a sample or a test reagent in the present apparatus as preliminary preparation before starting an analysis. More specifically, first, the buffer container and the positive buffer container 163 are filled with a buffer solution forming a part of the electrical path. The buffer solution is, for example, an electrolyte solution for the electrophoresis, which is commercially available.

Further, a sample to be analyzed is dispensed into wells of the sample container. The sample is a PCR product of a DNA, for example. In addition, a washing solution for washing the sample injection part 104 is dispensed into the washing container. The washing solution is pure water, for example. In addition, a separation medium for electrophoresing the sample is injected into the syringe 153. For example, the electrophoretic medium is a polyacrylamide-based separation gel for the electrophoresis, which is commercially available. In addition, in the case when the capillary 102 is expected to deteriorate or the length of the capillary 102 changes, the capillary array 101 is replaced. Then, when the preliminary preparation is completed, the operator operates the present apparatus and starts the analysis. The electrophoretic medium filling is a procedure of filling a new electrophoretic medium in the capillary 102 and forming the electrophoretic path.

In the electrophoretic medium filling of the present embodiment, first, the waste solution container is transported immediately below the sample injection part 104 by the auto sampler unit so that the waste solution container can receive the waste electrophoretic medium discharged from the sample injection end 105. Thereafter, the syringe 153 is driven to fill a new electrophoretic medium into the capillary 102, and the waste electrophoretic medium is disposed. Finally, the sample injection end 105 is immersed in the washing solution held in the washing container so as to wash the sample injection end 105 which became dirty due to the electrophoretic medium. The preliminary electrophoresis is a procedure of applying a predetermined voltage to the electrophoretic medium so as to make the electrophoretic medium suitable for the electrophoresis. In the preliminary electrophoresis of the present embodiment, first, the sample injection end 105 is immersed in the buffer solution held in the buffer container by using the auto sampler unit, and thus an electrical path is formed. Then, a voltage in the range of several to several tens of kilovolts is applied to the electrophoretic medium for several or several tens of minutes by the power supply unit, thereby making the electrophoretic medium suitable for the electrophoresis. Finally, the sample injection end 105 is immersed in the washing solution held in the washing container so as to wash the sample injection end 105 which became dirty due to the buffer solution. The sample injection is a procedure of injecting a sample component into the electrophoretic path.

In the sample injection of the present embodiment, first, the sample injection end 105 is immersed in the sample held within a well of the sample container by the auto sampler unit. As a result, an electrical path is formed, and thus the sample component is prepared to be injected into the electrophoretic path. Then, a pulse voltage is applied to the electrophoretic path by the power supply unit, and the sample component is injected into the electrophoretic path. Finally, the sample injection end 105 is immersed in the washing solution held in the washing container so as to wash the sample injection end 105 which became dirty due to the sample. The electrophoretic analysis is a procedure of separating and analyzing sample components contained in the sample by using an electrophoretic method. In the electrophoretic analysis of the present embodiment, first, the sample injection end 105 is immersed in the buffer solution held in the buffer container by the auto sampler unit, and thus an electrical path is formed.

Subsequently, a high voltage of about 15 kV is applied to the electrical path by the power supply unit so as to generate an electric field in the electrical path. Due to the electric field generated, each sample component in the electrophoretic path moves toward the irradiation part 103 at a speed depending on the property of each sample component. As a result, sample components are separated from one another by the difference of the moving speed. Then, the sample components are detected sequentially from a sample component reaching the irradiation part 103. For example, when the sample includes a plurality of DNAs whose base lengths are different from one another, the moving speeds of the sample components become different due to the difference in the base lengths, and as a result, the DNAs sequentially reach the irradiation part 103 in the order of a DNA whose base length is short. Therefore, by preparing a fluorescent material depending on a terminal base sequence for each DNA, it is possible to detect the terminal base sequence in the order of DNAs reaching the irradiation part 103. Then, a voltage application stops when intended data is obtained, and thus the electrophoretic analysis is completed. That is a series of analysis procedures. When another analysis is performed, the analysis procedure proceeds by starting to fill the electrophoretic medium.

First Embodiment

Figure 2:
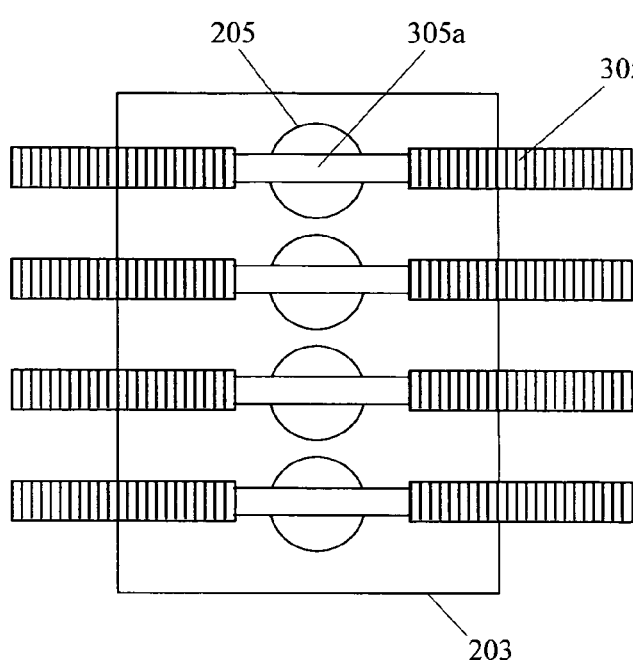
FIGS. 2A and 2B are views schematically illustrating an illumination optical system of the capillary electrophoretic apparatus according to the invention.
Figure 2:
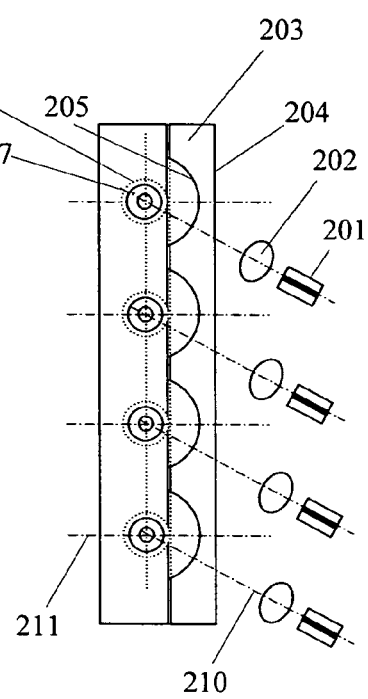

Hereinafter, an illumination optical unit of a capillary electrophoretic apparatus according to a first embodiment of the invention will be described with reference to FIGS. 2A and 2B. FIG. 2A is a plan view illustrating four capillaries 305 mounted on a glass substrate 203, and FIG. 2B is a cross-sectional view of FIG. 2A. The four capillaries 305 are arranged on the glass substrate 203 substantially in parallel and at predetermined intervals. At a portion where a polyimide film is removed of each of the capillaries 305, a capillary irradiation part 305a is located.

LED light irradiated from an LED light source 201 is condensed by a lens 202 and is then irradiated onto the capillary irradiation part 305a so as to cause a fluorescent dye of a sample to be excited. The fluorescent light output from the capillary irradiation part 305a is guided to a optical detection system provided at the opposite side of the light source 201. The optical detection system will be described hereinbelow.

The LED light source 201 is made such that, for example, a wavelength is 505 nm and an output is 1 mW. In addition, a laser may be used as a light source. The light sources 201 corresponding to the number of capillaries may be formed, or light emitted from one light source is split into four beams by a beam splitter and then each of the split beams is irradiated onto each capillary.

The glass substrate 203 has a function of a rear mirror and a function of a BP (band pass) optical filter. First, the function of the rear mirror will be described. On one surface of the glass substrate 203, a spherical surface 205 is formed. The spherical surface 205 is a reflective surface having a center on the capillary irradiation part 305a. The spherical surface 205 reflects fluorescent light returning from the capillary irradiation part 305a to the light source 201 and condenses the reflected fluorescent light onto the capillary irradiation part 305a. The reflected fluorescent light is guided to the optical detection system, which is provided at the opposite side of the light source 201, through the capillary irradiation part 305a, and the reflected fluorescent light causes the fluorescent dye in the capillary irradiation part 305a to be excited. Accordingly, the fluorescence intensity increases due to the stimulated emission effect.

Next, a function of the BP optical filter will be described. On the spherical surface 205 of the glass substrate 203 and a flat surface 204 opposite to the spherical surface 205 of the glass substrate 203, an interference filter serving as the BP optical filter is formed. The BP optical filter transmits only light within a predetermined wavelength range of the light emitted from the LED light source 201. That is, the BP optical filter guides only excitation light for exciting a fluorescent dye into the capillary irradiation part 305a and prevents light within the fluorescent wavelength range to be measured from reaching the capillary irradiation part 305a.

As shown in the figure, an optical axis 210 of the LED light source 201 is inclined at a predetermined angle with respect to a normal line of the flat surface 204 of the glass substrate 203, that is, an optical axis 211 of the optical detection system. Therefore, since reflected light flux from the flat surface 204 of the glass substrate 203 does not overlap incident light flux from the light source 201, it is possible to prevent the LED light source 201 from becoming unstable due to the returning light.

FIGS. 3A to 3D are views illustrating an example of an optical detection unit disclosed in JP-A No. 2004-144479. FIG. 3A is a cross-sectional view of the optical detection unit taken along a YZ plane, and FIG. 3B is a cross-sectional view of the optical detection unit taken along an XZ plane. The optical detection unit includes an LP optical filter 306, a first camera lens 301, a diffraction grating 302, a second camera lens 303, and a two-dimensional optical detector 304. The fluorescent light emitted from the capillary irradiation part 305a is incident on the first camera lens 301 through the LP optical filter 306 so as to be collimated light flux.

The collimated light flux is dispersed according to the wavelength by the diffraction grating 302 and an image generated by the wavelength-dispersed light is formed on the two-dimensional optical detector 304 by the second camera lens 303. Then, a signal output from the two-dimensional optical detector 304 is subjected to a computation process by a computer, and the sample is analyzed. Instead of the diffraction grating 302, a wavelength dispersion unit may be formed by a proper combination of a prism or a filter. In addition, although a CCD camera is generally used as the two-dimensional optical detector 304, one-dimensional detector, a photomultiplier, or a photodiode may be properly combined with an optical mechanism.

The LP optical filter 306 shields light having a wavelength shorter than that of fluorescent light to be measured. In other words, the LP optical filter 306 prevents excitation light, which is very strong as compared with the fluorescent light, from reaching the two-dimensional optical detector 304.

As shown on right sides of FIGS. 3A and 3B, the capillaries 305 extend in parallel to an X axis and are arranged at predetermined intervals along the Y-axis direction. Accordingly, an electrophoretic direction E is an X-axis direction. In a conventional optical detection unit, as shown in FIG. 3C, rulings 401 of the diffraction grating 302 extend in parallel to the Y axis and are arranged at predetermined small intervals along the X-axis direction. Accordingly, the fluorescent light emitted from the capillary irradiation part 305a is wavelength-dispersed in the X-axis direction. That is, a wavelength dispersion direction W is the X-axis direction.

As shown in FIG. 3D, on an image 501 obtained by the two-dimensional optical detector 304, four emission spectrums 601 indicating fluorescent light emitted from four capillaries are displayed at predetermined intervals along the Y-axis direction. The spacing between the four emission spectrums 601 in the Y-axis direction corresponds to a spacing between the four capillaries in the Y-axis direction. Each of the four emission spectrums 601 extends from red to blue components in the X-axis direction, as shown in FIG. 3D. That is, a wavelength dispersion direction W is the X-axis direction equal to the electrophoretic direction E.

Figure 8:
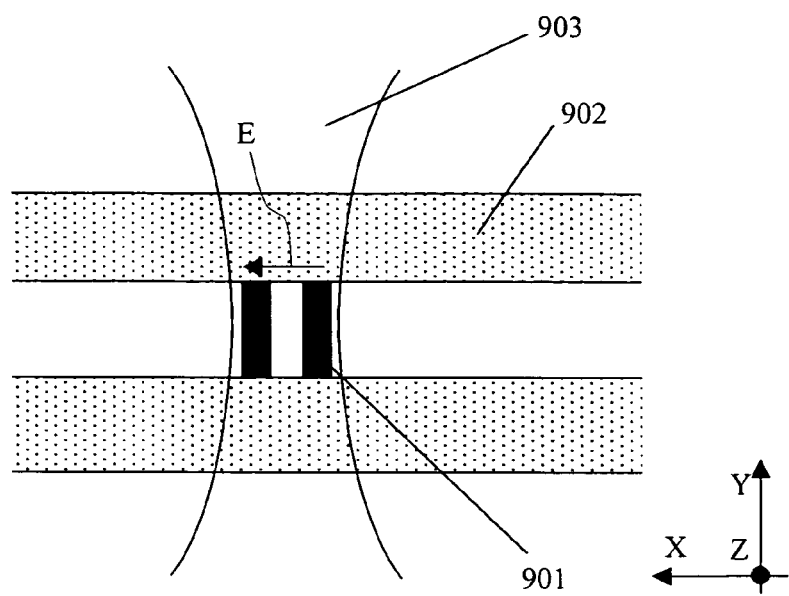
FIGS. 8A and 8B are views explaining a mechanism in which a quasi peak occurs.
Figure 8:
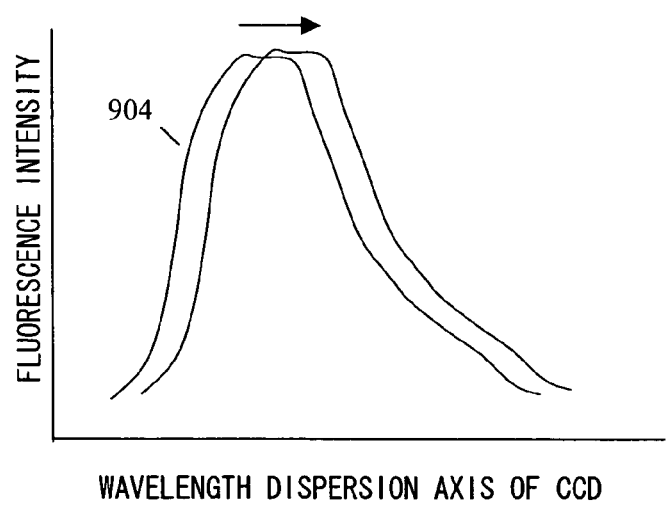

FIG. 8A illustrates a state in which a DNA band 901 separated by electrophoresis moves within a capillary 902. Onto an irradiation part of the capillary 902, condensed excitation light 903 is irradiated, and the excitation light 903 has a predetermined width. Therefore, while the DNA band 901 comes into a region where the excitation light 903 is irradiated and comes out therefrom, a signal obtainable by the two-dimensional detector 304 is changed.

As described above, since the electrophoretic direction E is equal to the wavelength dispersion direction W, the DNA band 901 moves in the wavelength dispersion direction W while the DNA band 901 passes through the region where the excitation light 903 is irradiated. As a result, as shown in FIG. 8B, the wavelength of an emission spectrum 904 obtainable by the two-dimensional detector 304 is substantially changed. This generates the same effect as in a case in which the wavelength of an emission spectrum changes over time while the DNA band 901 passes through the excitation light 903. In the electrophoretic method, a plurality of fluorescent dyes is used, and the plurality of fluorescent dyes corresponds to four kinds of bases, respectively. Accordingly, if the emission spectrum is substantially changed, it becomes difficult to make an observed emission spectrum completely correspond to various fluorescent dyes or various bases. That is, when each base corresponds to each component of the emission spectrum, a residual component (quasi peak) that does not correspond to a base is generated.

FIGS. 4A to 4D illustrate an optical detection unit of the capillary electrophoretic apparatus according to the first embodiment of the invention. FIG. 4A is a cross-sectional view of the optical detection unit taken along a XZ plane, and FIG. 4B is a cross-sectional view of the optical detection unit taken along an YZ plane. In the invention, the movement direction of a DNA band, that is, an electrophoretic direction E is set to be orthogonal to a wavelength dispersion direction W. Specifically, as shown in FIG. 4C, rulings 402 of the diffraction grating 302 extend in parallel to X axis and are arranged at predetermined small intervals along Y axis. Therefore, fluorescent light emitted from the capillary irradiation part 305a is dispersed according to the wavelength in the Y-axis direction. Since the movement direction of the DNA band is in the X-axis direction, the movement direction of the DNA band is orthogonal to the wavelength dispersion direction W. As a result, as shown in FIG. 4D, on an image 502 obtained by the two-dimensional optical detector 304, four emission spectrums 602 indicating fluorescent light emitted from four capillaries are displayed at predetermined intervals along the Y-axis direction. The spacing between the four emission spectrums 602 in the Y-axis direction corresponds to an arrangement pitch between the four capillaries 305. Each of the four emission spectrums 602 extends from red to blue components in the Y-axis direction. The four emission spectrums 602 overlap each other in the Y-axis direction so as to be displayed. In addition, even though the four emission spectrums 602 moves on the image 502 in the X direction while the DNA band 901 passes through a region where the excitation light 903 is irradiated, the wavelength dispersion direction does not change in the wavelength dispersion direction. As a result, since the emission spectrum is not substantially changed, it is possible to prevent the quasi peak from occurring.

Second Embodiment

Figure 5:
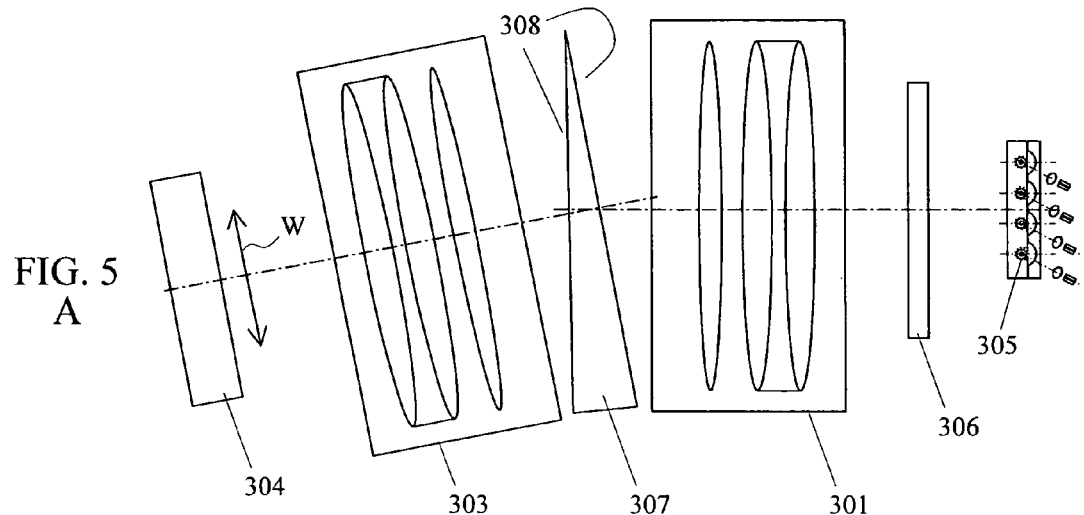
FIGS. 5A and 5B are views illustrating the relationship between the configuration of a optical detection system and an image on a two-dimensional detector in a capillary electrophoretic apparatus according to a second embodiment of the invention.
Figure 5:
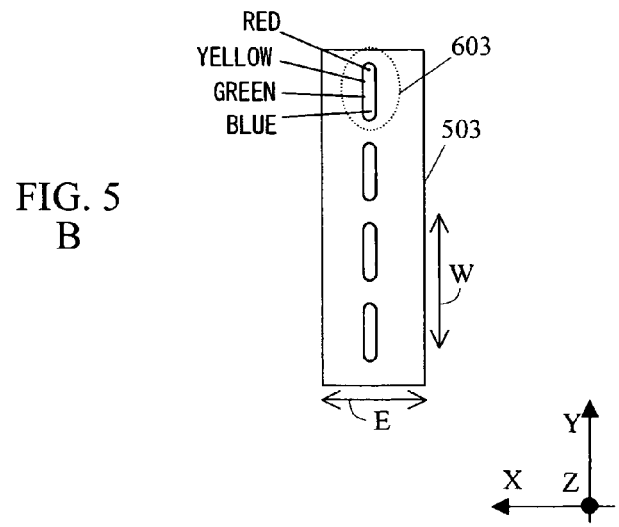

An optical detection unit of a capillary electrophoretic apparatus according to a second embodiment of the invention will be described with reference to FIGS. 5A and 5B. FIG. 5A is a cross-sectional view of the optical detection unit according to the present embodiment, which is taken along a YZ plane. In the embodiment shown in FIGS. 4A to 4D, since the four emission spectrums corresponding to the four capillaries overlap each other, it is difficult to read out the emission spectrum from each capillary. For this reason, in the present embodiment, a prism 307 instead of the diffraction grating 302 effects the wavelength dispersion. The wavelength dispersion power of the prism 307 is smaller than that of the diffraction grating 302. Accordingly, as shown in FIG. 5B, on an image 503 obtained by the two-dimensional optical detector 304, four emission spectrums 603 indicating fluorescent light emitted from four capillaries do not overlap each other because the length of each of the emission spectrums 603 extending from red to blue components become short. As a result, it is possible to read out each of the four emission spectrums 603. In addition, an anti-reflection film 308 is formed on a surface of the prism 307 so that stray light due to multiple reflections is not generated.

Third Embodiment

Figure 6A:
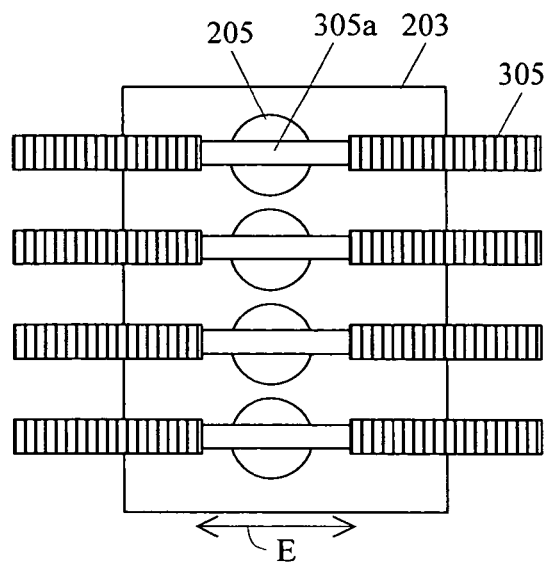
FIGS. 6A to 6C are views illustrating the relationship between the configuration of a optical detection system and an image on a two-dimensional detector in a capillary electrophoretic apparatus according to a third embodiment of the invention.
Figure 6B:
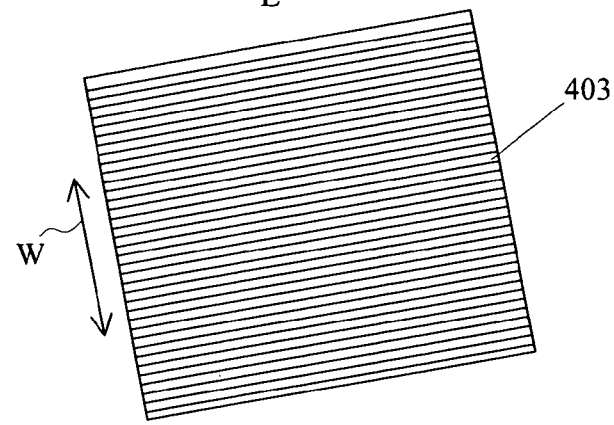
Figure 6C:
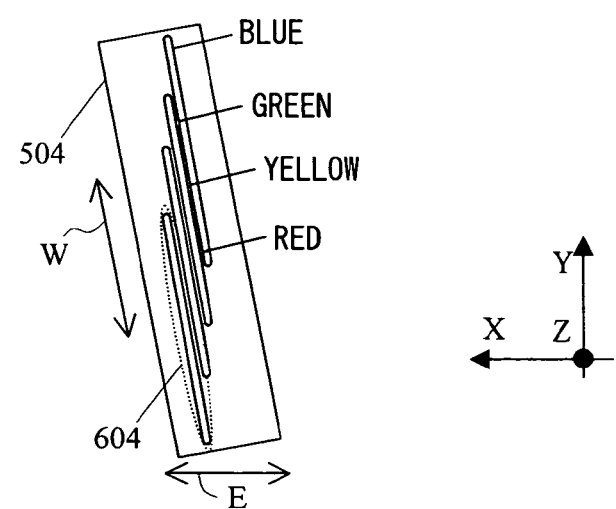

An optical detection unit of a capillary electrophoretic apparatus according to a third embodiment of the invention will be described with reference to FIGS. 6A to 6C. FIG. 6A illustrates a state in which the four capillaries 305 extend on the glass substrate 203 in parallel to the X axis and are arranged at predetermined intervals along the Y-axis direction, in the same manner as in FIG. 2A. FIG. 6B shows the diffraction grating 302 and the direction of rulings 403. In the present embodiment, as compared with the first embodiment shown in FIG. 4C, the diffraction grating 302 and the rulings 403 are slightly inclined. That is, the rulings 403 of the diffraction grating 302 extend in a direction slightly inclined with respect to the X-axis direction and are arranged at predetermined intervals along a direction slightly inclined with respect to the Y-axis direction. As a result, the wavelength dispersion direction W is not completely vertical but approximately vertical to the capillaries 305. Since the capillaries 305 extend in the X-axis direction, the wavelength dispersion direction W is slightly inclined with respect to the Y-axis direction. As shown in FIG. 6C, on an image 504 obtained by the two-dimensional optical detector 304, four emission spectrums 604 indicating fluorescent light emitted from the four capillaries are slightly inclined and are slightly deviated from each other along the Y-axis direction. As a result, the four emission spectrums 604 do not overlap each other.

In the present embodiment, the fluorescent light emitted from the capillaries is dispersed according to the wavelength by the diffraction grating 302. Accordingly, the obtainable emission spectrum 604 is sufficiently long.

Further, in the present embodiment, since the wavelength dispersion direction W is set to be approximately vertical to the electrophoretic direction E, the moving distance of the emission spectrum moving in the wavelength dispersion direction is very small while the DNA band passed through a region where the excitation light is irradiated. As a result, it is possible to prevent the quasi peak from occurring.

Fourth Embodiment

Figure 7:
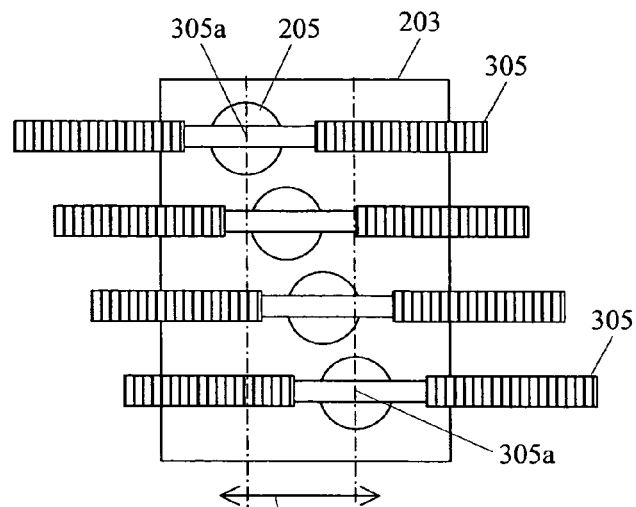
FIGS. 7A to 7C are views illustrating the relationship between the configuration of a optical detection system and an image on a two-dimensional detector in a capillary electrophoretic apparatus according to a fourth embodiment of the invention.
Figure 7:
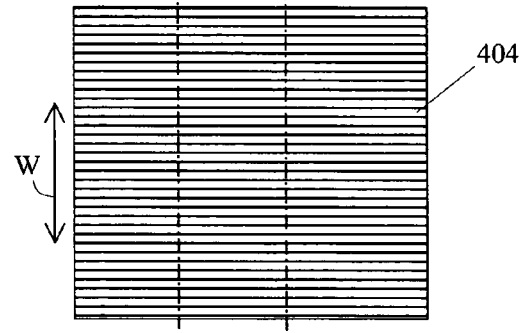
Figure 7:
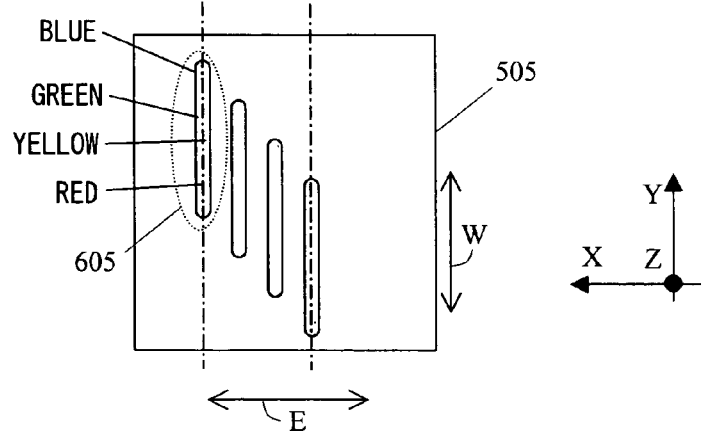

An optical detection unit of a capillary electrophoretic apparatus according to a fourth embodiment of the invention will be described with reference to FIGS. 7A to 7C. As shown in FIG. 7A, in the present embodiment, the irradiation parts 305a of the four capillaries 305 are disposed to be deviated from each other in the X-axis direction. As shown in FIG. 7B, the wavelength dispersion direction W is in the Y-axis direction in the same manner as in FIG. 4C. That is, rulings 404 of the diffraction grating 302 extend in parallel to the X-axis direction and are arranged at predetermined small intervals along the Y-axis direction.

As shown in FIG. 7C, on an image 505 obtained by the two-dimensional optical detector 304, four emission spectrums 605 indicating fluorescent light emitted from the four capillaries are displayed at predetermined intervals along the X-axis and Y-axis directions. Each of the four emission spectrums 605 extends from red to blue components in the Y-axis direction, as shown in FIG. 7C. The spacing between the four emission spectrums 605 in the X-axis direction corresponds to the deviation amount between the irradiation parts 305a of the four capillaries 305 in the X-axis direction. The spacing between the four emission spectrums 605 in the Y-axis direction corresponds to an arrangement pitch between the four capillaries 305.

In the present embodiment, the distances from the sample injection ends of the four capillaries to the capillary irradiation parts 305a, that is, the electrophoretic length are different from each other. The differences among the electrophoretic lengths in the four capillaries correspond to the deviation amount between the irradiation parts 305a of the four capillaries 305 in the X-axis direction.

By making the deviation amount between the irradiation parts 305a of the four capillaries 305 in the X-axis direction sufficiently small, the differences among the electrophoretic lengths can become sufficiently small. As a result, it is possible to reduce a detection error due to the differences among the electrophoretic lengths. In addition, in the case in which the detection error due to the differences among the electrophoretic lengths cannot be ignored, the difference among the electrophoretic lengths can be corrected by calibrating electrophoretic time and the length of a DNA for each capillary. Alternatively, the electrophoretic length can be accurately adjusted by adjusting a loose part of a capillary located somewhere within a range from the sample injection end to the capillary irradiation part 305a.

Fifth Embodiment

In a fifth embodiment, a method of irradiating excitation light is changed so as to irradiate a spread beam such that a plurality of capillaries can be irradiated. Hereinafter, it will be primarily described with respect to different points between the fifth embodiment and the first to fourth embodiments.

In the present embodiment, laser beams emitted from a laser light source are dispersed by a beam expander, converged in a line shape by a cylindrical lens, and are simultaneously irradiated onto all capillaries from a direction vertical to an arrangement plane of the capillaries. Thereby, regardless of the deviation among capillaries, all of the capillaries can be irradiated with approximately the same laser intensities.

Sixth Embodiment

In a sixth embodiment, a method of irradiating excitation light is changed so as to irradiate a laser beam such that a plurality of capillaries can be scanned. Hereinafter, it will be primarily described with respect to different points between the sixth embodiment and the first to fifth embodiments. In the present embodiment, laser beams emitted from a laser light source are reflected by a mirror, are condensed by an object lens, and are irradiated onto a laser irradiation location of each capillary. The mirror and the object lens form a driving unit and are reciprocally driven at high speed and in the same direction as an arrangement direction of capillaries. As such, the respective capillaries can be sequentially scan-irradiated with laser beams.

While the invention has been described with reference to exemplary embodiments thereof, it will be understood by those skilled in the art that various changes and modifications may be made without departing from the scope of the invention as defined by the following claims.

What is claimed is:
1. An electrophoretic apparatus comprising:
a plurality of electrophoretic paths;
an irradiation unit that irradiates excitation light onto the electrophoretic paths arranged at predetermined intervals therebetween;
a wavelength dispersion unit that disperses fluorescent light output from the electrophoretic paths according to the wavelength; and
an optical detection unit that detects light from the wavelength dispersion unit so as to obtain an emission spectrum, wherein:
a wavelength dispersion direction of the wavelength dispersion unit is slightly inclined with respect to a direction perpendicular to an electrophoretic direction in each of the electrophoretic paths,
the wavelength dispersion unit disperses the fluorescent light according to the wavelength such that a plurality of emission spectrums corresponding to the plurality of electrophoretic paths do not overlap each other and are substantially positioned along a straight line in the wavelength dispersion direction, the plurality of emission spectrums are adjacent to each other in series along the same straight line in the wavelength dispersion direction and are slightly inclined and slightly deviated from each other, the irradiation positions of the excitation light in the plurality of electrophoretic paths are deviated from each other along the electrophoretic direction, and the wavelength dispersion unit is arranged so as to be perpendicular to an emission line of the fluorescent light.

2. The electrophoretic apparatus according to claim 1, wherein the wavelength dispersion unit is a prism.

3. The electrophoretic apparatus according to claim 1, wherein the wavelength dispersion unit is a diffraction grating.

4. The electrophoretic apparatus according to claim 1, wherein the electrophoretic paths are capillaries.

5. The electrophoretic apparatus according to claim 1, wherein the excitation light is irradiated so as to sequentially propagate to the adjacent electrophoretic paths.

6. An electrophoretic method comprising:

electrophoresing a plurality of fluorescently marked samples by using a plurality of electrophoretic paths;

irradiating excitation light onto the plurality of electrophoretic paths arranged at predetermined intervals therebetween;

dispersing, via a wavelength dispersion unit, fluorescent light output from the electrophoretic paths according to the wavelength, in a direction slightly inclined with respect to a direction perpendicular to an electrophoretic direction in each of the electrophoretic paths, wherein the wavelength dispersion unit is arranged so as to be perpendicular to an emission line of the fluorescent light; and detecting the wavelength-dispersed light so as to obtain an emission spectrum, wherein:

the fluorescent light is dispersed according to the wavelength such that a plurality of emission spectrums corresponding to the plurality of electrophoretic paths do not overlap each other and are substantially positioned along a straight line in the wavelength dispersion direction, the plurality of emission spectrums are adjacent to each other in series along the same straight line in the wavelength dispersion direction and are slightly inclined and slightly deviated from each other, and the irradiation positions of the excitation light in the plurality of electrophoretic paths are deviated from each other along the electrophoretic direction.

7. The electrophoretic method according to claim 6, wherein the excitation light is irradiated so as to sequentially propagate to the adjacent electrophoretic paths.

8. The electrophoretic apparatus according to claim 1, wherein the wavelength dispersion unit disperses the fluorescent light output from each of the electrophoretic paths according to the wavelength to generate a continuous spectrum of fluorescent light for each of the electrophoretic paths.

9. The electrophoretic method according to claim 6, wherein the fluorescent light output from each of the electrophoretic paths is dispersed according to the wavelength to generate a continuous spectrum of fluorescent light for each of the electrophoretic paths.

* * * * *